(12) United States Patent
Zajdband et al.

(10) Patent No.: US 11,984,197 B2
(45) Date of Patent: May 14, 2024

(54) MICROBIAL QUANTITATION

(71) Applicant: Trace Genomics, Inc., Burlingame, CA (US)

(72) Inventors: Ariel David Zajdband, Berkeley, CA (US); Wyatt Hugh Hartman, San Francisco, CA (US); David Curtis Stone, San Francisco, CA (US); Rosaria Chiang, Redwood City, CA (US)

(73) Assignee: TRACE GENOMICS, INC., Ames, IA (US)

( * ) Notice: Subject to any disclaimer, the term of this patent is extended or adjusted under 35 U.S.C. 154(b) by 1016 days.

(21) Appl. No.: 16/892,093

(22) Filed: Jun. 3, 2020

(65) Prior Publication Data
US 2020/0381081 A1    Dec. 3, 2020

Related U.S. Application Data

(60) Provisional application No. 62/856,429, filed on Jun. 3, 2019.

(51) Int. Cl.
| | |
|---|---|
| *C12Q 1/6869* | (2018.01) |
| *C12N 1/06* | (2006.01) |
| *C12Q 1/06* | (2006.01) |
| *G01N 33/24* | (2006.01) |

(Continued)

(52) U.S. Cl.
CPC ........... *G16B 30/00* (2019.02); *C12N 1/06* (2013.01); *C12Q 1/06* (2013.01); *C12Q 1/6869* (2013.01); *G01N 33/24* (2013.01); *G16B 35/20* (2019.02); *G01N 2033/243* (2013.01)

(58) Field of Classification Search
CPC ... C12N 1/00; C12N 1/02; C12N 1/06; G16B 30/00; G16B 35/20
See application file for complete search history.

(56) References Cited

U.S. PATENT DOCUMENTS

| | | | |
|---|---|---|---|
| 6,570,999 B1 | 5/2003 | Monson | |
| 11,821,887 B2 * | 11/2023 | Parameswaran | ..... C12Q 1/6895 |
| 2009/0075274 A1 | 3/2009 | Slepnev et al. | |

(Continued)

OTHER PUBLICATIONS

PCT International Search Report and Written Opinion, PCT Application No. PCT/US2020/035961, dated Sep. 18, 2020, 15 pages.

(Continued)

*Primary Examiner* — Lam S Nguyen
(74) *Attorney, Agent, or Firm* — Fenwick & West LLP

(57) ABSTRACT

In various embodiments of an analytics system, a spike-in including synthetic constructs of nucleic acid is added to soil samples for processing. The analytics system determines sequence reads classified to a microbe in the soil sample. The analytics system determines one or more measures of soil texture of the soil sample, for example, indicating percentages of sand, silt, and clay. The analytics system determines a measure of the microbe as a function of at least the classified sequence reads, the one or more measures of soil texture, and a mass of the spike-in. The analytics system can transmit the measure of the microbe to a client device for display on a user interface. A field where the soil sample was obtained can be treated according to the measure of the microbe.

20 Claims, 14 Drawing Sheets

(51) Int. Cl.
  *G16B 30/00* (2019.01)
  *G16B 35/20* (2019.01)

(56) References Cited

U.S. PATENT DOCUMENTS

| | | | |
|---|---|---|---|
| 2009/0188290 A1 | 7/2009 | Marler | |
| 2017/0370213 A1 | 12/2017 | Knight et al. | |
| 2019/0194742 A1* | 6/2019 | Wu | G16B 40/00 |
| 2019/0227046 A1 | 7/2019 | Parameswaran et al. | |
| 2020/0271636 A1* | 8/2020 | Hartman | G01N 33/24 |

OTHER PUBLICATIONS

Thies, J. E. "Chapter 6: Molecular Approaches to Studying the Soil Biota." Soil Microbiology, Ecology, and Biochemistry, Elsevier, Inc., 2015, pp. 151-185.

Vishnivetskaya, T. et al. "Commercial DNA Extraction Kits Impact Observed Microbial Community Composition in Permafrost Samples." FEMS Microbiology Ecology, vol. 87, No. 1, Jan. 2014, pp. 217-230.

European Patent Office, Extended European Search Report, EP Patent Application No. 20819172.6, dated Jun. 2, 2020, 9 pages.

Hardwick, S. A., et al., "Synthetic microbe communities provide internal reference standards for metagenome sequencing and analysis", Nature Communications, vol. 9, No. 1, Aug. 6, 2018, pp. 1-10.

Stämmler, F., et al., "Adjusting microbiome profiles for differences in microbial load by spike-in bacteria", Microbiome, vol. 4, No. 1, 21 Jun. 21, 2016, pp. 1-13.

Tourlousse, D. M., et al., "Synthetic spike-in standards for high-throughput 16S rRNA gene amplicon sequencing", Nucleic Acids Research, vol. 45, No. 4, Dec. 15, 2016, pp. 1-14.

Wolinska, A., et al., "Metagenomic 1-15 Analysis of Some Potential Nitrogen-Fixing Bacteria in Arable Soils at Different Formation Processes", Microbial Ecology, vol. 73, No. 1, Aug. 31, 2016, pp. 162-176.

* cited by examiner

200

```
Determine sequence reads of a soil sample to which is
added synthetic nucleic acids
202
          │
          ▼
Classify the sequence reads
204
          │
          ▼
Assign a soil texture label
206
          │
          ▼
Determine a measure of an amount of a microbe
208
          │
          ▼
Transmit the measure to a client device for display on a
user interface
210
          │
          ▼
┌ ─ ─ ─ ─ ─ ─ ─ ─ ─ ─ ─ ─ ─ ─ ─ ─ ─ ─ ┐
│ Treat soil according to the measure │
│ 212                                  │
└ ─ ─ ─ ─ ─ ─ ─ ─ ─ ─ ─ ─ ─ ─ ─ ─ ─ ─ ┘
```

Xanthomonas vasicola pv. vasculorum
Crop: Corn
Grouping: Sample
Threshold: 0.60 PPB soil

MICROBIAL QUANTITATION

CROSS REFERENCE TO RELATED APPLICATION

This application claims the benefit of priority to U.S. Provisional Application No. 62/856,429, filed on Jun. 3, 2019, which is incorporated herein by reference in its entirety for all purposes.

TECHNICAL FIELD

This disclosure generally relates to enumeration of microbial taxa and genes in, e.g., agricultural soils, by sequencing and an internal reference standard.

BACKGROUND

The soil microbiomes (and microbiomes in other environments) include thousands of organisms, including bacteria, fungi, nematodes, and insects, among other microbes. Metagenomics (also referred to as environmental genomics or community genomics) may involve developing a profile of the microbiome detected in a biological sample such as soil. As one application, it is desirable to predict whether a farmer's field will produce a high or low crop yield, and whether the crops will develop disease. Further, it is challenging to determine the impact of microbe species (e.g., in soil) on crop yield and disease pressure.

BRIEF DESCRIPTION OF THE FIGURES

The disclosed embodiments have advantages and features which will be more readily apparent from the detailed description, the appended claims, and the accompanying figures (or drawings). A brief introduction of the figures is below.

FIG. 2A illustrates an example process for determining metrics of a soil sample according to various embodiments of the present invention.

FIG. 10 is a diagram indicating microbial quantitation of a pathogen according to various embodiments of the present invention.

SUMMARY

Figure 1:
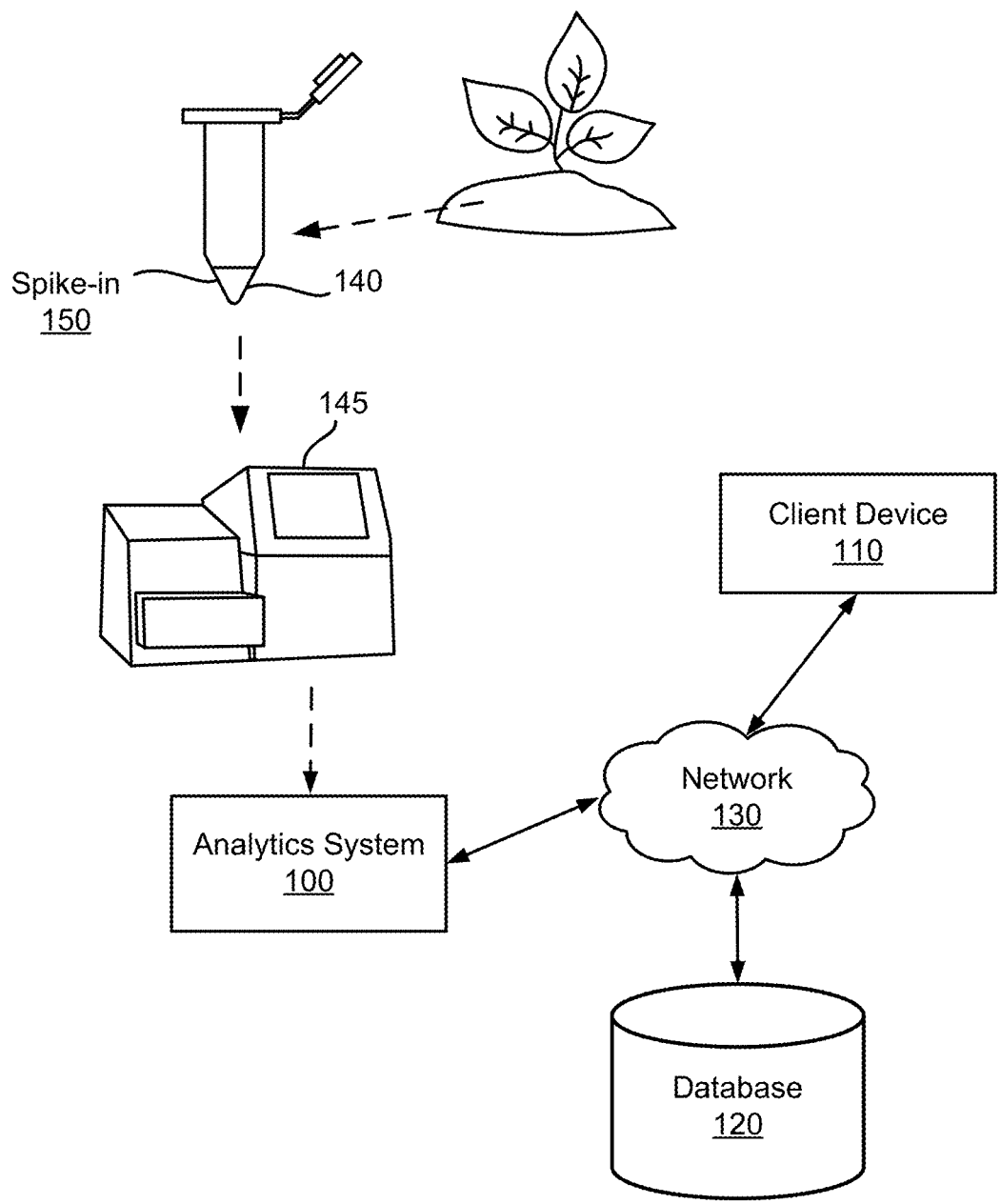
FIG. 1 illustrates an example system environment for an analytics system according to various embodiments of the present invention.

In various embodiments, a method includes determining a plurality of sequence reads of a soil sample to which is added one or more synthetic nucleic acids. The method further includes classifying a subset of the plurality of sequence reads into one or more subsets, each subset matched to a particular microbe present in the soil sample. The method further includes assigning to the soil sample a soil texture label according to one or more measures of soil texture of soil in the soil sample. The method further includes determining a measure of an amount of a microbe within the soil sample as a function of at least a subset of the plurality of sequence reads matched to the microbe, the soil texture label assigned, and a mass of the one or more synthetic nucleic acids present in the soil sample. The method further includes transmitting the measure of the microbe within the soil sample to a client device for display on a user interface.

In some embodiments, assigning to the soil sample the soil texture label comprises: determining a first percentage of sand in the soil sample; determining a second percentage of silt in the soil sample; and determining a third percentage of clay in the soil sample, wherein the first percentage, second percentage, and third percentage sum to 100%.

In some embodiments, determining the measure of the amount of the microbe comprises: normalizing the measure of the amount of the microbe according to dry mass content of the soil sample.

In some embodiments, the method further includes performing cell lysis on the soil sample after the one or more synthetic nucleic acids has been added and before determining the plurality of sequence reads of the soil sample. In some embodiments, the one or more synthetic nucleic acids includes a plurality of synthetic nucleic acids each at different a concentration.

In some embodiments, the measure of the amount of the microbe is a genomic mass of the microbe per a unit of mass of the soil sample, and wherein determining the measure of the amount of the microbe comprises: determining a ratio of a first number of sequence reads in the subset of the plurality of sequence reads matched to the microbe to a second number of sequence reads of the plurality of sequence reads matched to the one or more synthetic nucleic acids.

In some embodiments, the ratio includes at least one correction factor accounting for underrepresented organism abundances. In some embodiments, the at least one correction factor is based on whether the organism has a cell wall. In some embodiments, the at least one correction factor is based on cell lysis efficiency or classification efficiency.

In some embodiments, the measure of the amount of the microbe is a cell count of the microbe in the soil sample per gram of the soil sample. In some embodiments, the method further includes treating a field where the soil sample was obtained according to the measure of the amount of the microbe. In some embodiments, the method further includes determining a total biomass of microbial genetic material present in the soil sample by measuring amounts of a plurality of microbes present in the soil sample.

In various embodiments, a system includes a sampling tube for obtaining a soil sample to which is added one or more synthetic nucleic acids; and a non-transitory computer readable storage medium having instructions that when executed by one or more processors cause the one or more processors to perform steps of any of the above described methods.

Definitions

Unless defined otherwise, all technical and scientific terms used herein have the meaning commonly understood by a person skilled in the art to which this description belongs. As used herein, the following terms have the meanings ascribed to them below.

The term "microbe" refers to microorganisms including bacteria, pathogens, archaea, fungi, algae, protozoa, viruses, nematodes, and insects.

The term "sample" refers to matter obtained from an ecosystem that includes at least some biological material, such as microbes. Throughout the description, examples are given that relate to "soil samples," but embodiments of the invention can apply to microbiomes in other environments and non-soil sample types as well (e.g., aquatic environment microbiomes, human body microbiomes, or microbiomes of other organisms, etc.).

The term "sequence read" refers to a nucleotide sequence of a nucleic acid or nucleic acid fragment (e.g., DNA or RNA) read from a soil sample. Sequence reads can be obtained through various methods known in the art. Sequence reads can be classified according to the known organism from which they originate using genomic reference databases.

The term "spike-in" refers to a nucleic acid added to a soil sample, such as a synthetic nucleic acid including one or more artificially constructed or modified nucleic acids. One example is a synthetic plasmid spike in that is added to a soil aliquot in a sample tube.

DETAILED DESCRIPTION

In various embodiments of an analytics system for microbial quantitation, a spike-in is added to soils or samples containing soils (including slurries or other soil mixtures) prior to nucleic acid extraction and sequencing, to determine relative abundance data for the nucleic acid present prior to nucleic acid extractions. The analytics system can use information from sequencing and an internal reference standard (including correction factors, e.g., lysis and classification efficiency) to enumerate microorganism and/or functional gene abundances in soils, as related to agricultural productivity and management decisions. The analytics system can use additional experimental data to validate the quantitative approach and calibrate enumerations. The analytics system can use further experimental data to account or correct for variable cell lysis efficiencies and/or bioinformatics classification rates, among other types of sources of error.

The analytics system may output gene counts or a measure of an organism in nanograms (ng) DNA/gram (g) of soil. The analytics system may use additional information on the number of ng DNA/genome/organism to derive organism cell counts per gram of soil. The analytics system may use organism mass information to determine, for example, disease thresholds for soil nematodes or other soil borne pathogens, or masses of functional genes to inform management of soil nutrient processing, or thresholds for beneficial organisms. In some embodiments, known microorganisms alien to soils (or their genomic DNA) may be used as an alternative to a DNA synthetic construct.

Figure 3:
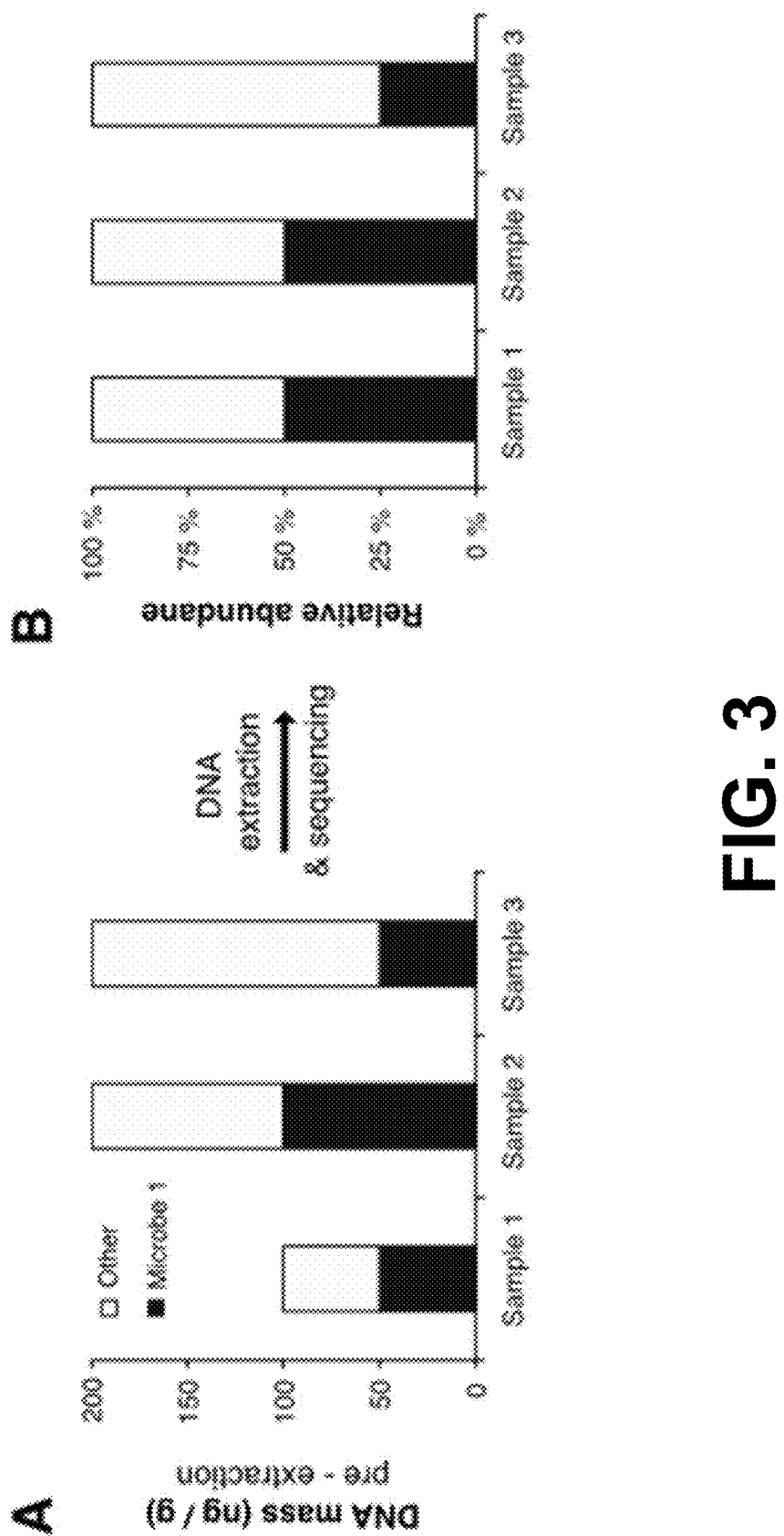
FIG. 3 is a diagram of relative abundance data of microbes in soil samples.
Figure 6:
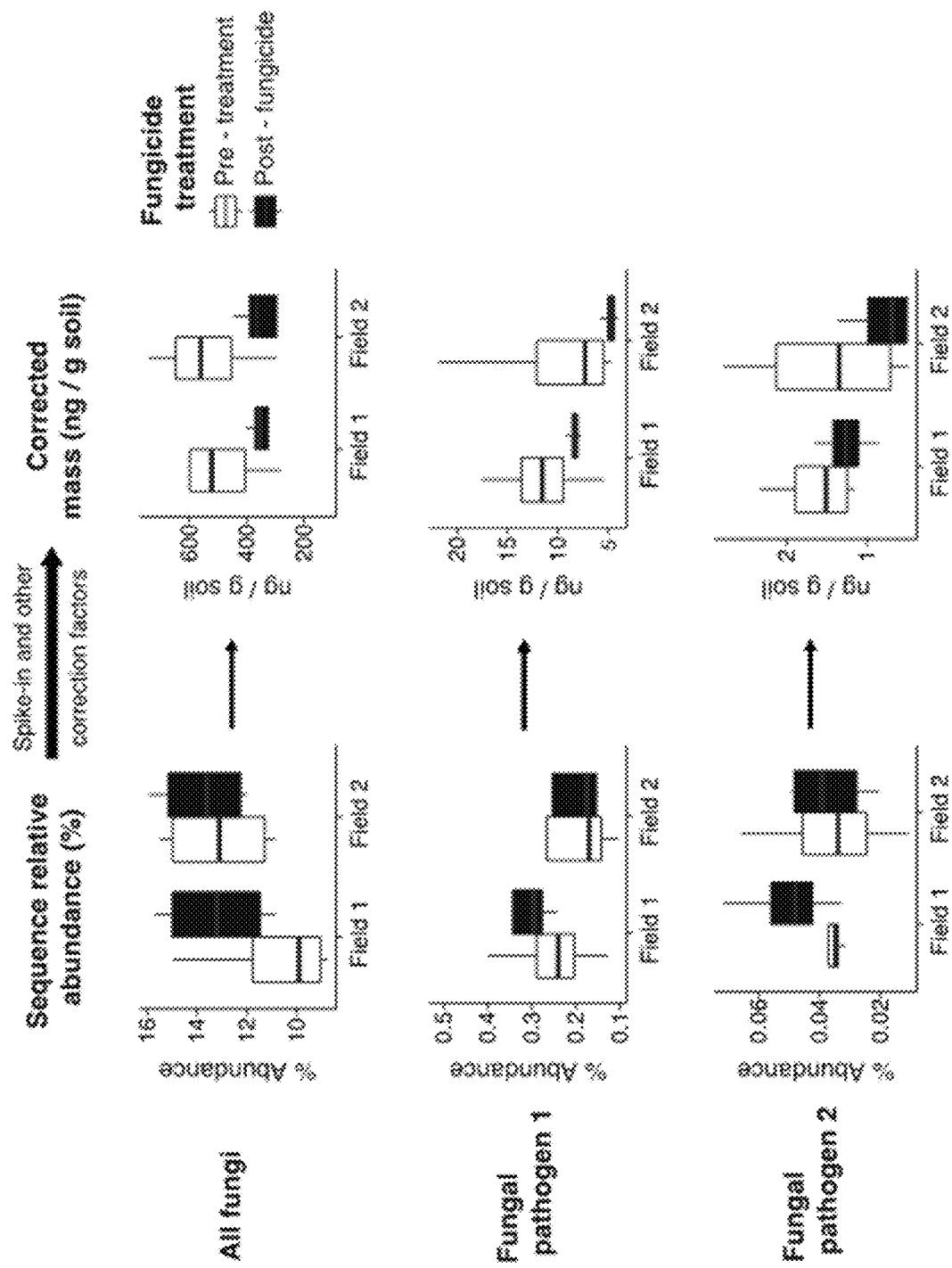
FIG. 6 is a diagram illustrating that calculation of organism mass in soils from corrected sequence data shows the effect of fungicide on soil fungi and specific fungal plant pathogens according to various embodiments of the present invention.

DNA sequencing for the identification of microorganisms or functional genes in a soil sample yields a large pool of identified sequence reads. Using sequencing may enable determination of the relative abundance of a given organism or gene (e.g., percentage of total reads). However, such data may not necessarily be adequate to represent the absolute abundance of organisms in a given unit of soil (e.g., by mass or volume), given variation in DNA mass initially present in the sample. For example, in two soil samples, the relative abundance of a plant pathogen may be 1% for each. However, if the first sample has only a tenth of the biomass of the second sample, relative abundance data alone will mask the fact that there are ten times as many pathogens in the second sample available to infect a host crop plant. For example, see FIG. 3 illustrating this. This discrepancy may arise when comparing effects of a fungicide treatment in an agricultural soil. In particular, the relative abundances of fungal pathogens may not change significantly or may actually increase after fungicide application, while the absolute abundances of the pathogens were significantly reduced. For example, see FIG. 6 illustrating this.

Embodiments of the present invention provide advantages over conventional systems that determine direct enumeration of microbial cell counts (of whole communities) by methods such as: flow cytometry (not scalable, low throughput), microbial biomass carbon or PLFA masses (not accurate or proportionate to DNA), or qPCR to enumerate marker gene masses in soil or microbiome DNA extracts (reflects post-extraction DNA mass, therefore subject to known variation in extraction efficiency among soil types).

In various embodiments, the analytics system estimates nanogram (ng) DNA/gram (g) soil for each organism or gene, rather than proportional relative abundance read counts. The analytics system can use errors in estimated data from experiments to derive correction factors for lysis efficiencies. The analytics system can correct for overall sequence classification rates in metagenomic (shotgun sequencing) data, and may apply organism-specific corrections based on empirical or in-silico sequence data. The analytics system can correct or provide more accurate microbiome read abundance data to absolute organism or gene amounts in ng DNA/g soil (or organisms/g soil) in order to inform agronomic management decisions including but not limited to management of soil pathogens, soil beneficial organisms, element cycling or fertility.

I. EXAMPLE SYSTEM OVERVIEW

FIG. 1 illustrates an example system environment for an analytics system 100 according to an embodiment. The system environment shown in FIG. 1 includes the analytics system 100, a client device 110, and a database 120, which are connected to each other via a network 130 (e.g., the Internet). In other embodiments, different or additional entities can be included in the system environment. For instance, the system environment may include a sequencer 145 to process one or more samples 140. Though only one client device 110 and database 120 is shown in FIG. 1, the system environment may include additional client devices 110 and/or databases 120. The functions performed by the various entities of FIG. 1 may vary in different embodiments.

The sequencer 145 performs sequencing (e.g., of DNA and/or RNA) and outputs sequence reads of the sample 140, which can be applied with a spike-in 150. The sequencer 145 may provide the output sequence reads to the analytics system 100. The sequencer 145 can be communicatively coupled to the analytics system 100 through a wireless, wired, or a combination of wireless and wired communication technologies. The analytics system 100 may use the sequence reads to identify presence or measure of one or more particular organisms in the soil from which the sample 140 was obtained. Additionally, the analytics system 100 may use these measures for any of the methods or processes described herein.

The analytics system 100 can determine metrics of soil samples using soil health indicators. A soil health indicator is defined as a value of microbial driven function pertinent to agricultural production. A soil health indicator may reflect soil mineral and organic element availability, plant growth promoting factors, interaction with plant pathogens, crop performance, or other indicators of soil function or health. A soil health indicator may be derived by processing nucleic acids of a soil sample, for example, by sequencing deoxyribonucleic acid (DNA) or ribonucleic acid (RNA) to determine composition of microbes (also referred to herein as microorganisms or organisms) present in the soil sample, i.e., "microbial composition." Soil health indicators may be used to predict physical attributes of crops (e.g., stem size, plant height, or fruit size), crop yield, or resistance or crops or soil to certain diseases or pests.

The analytics system 100 may obtain soil samples (or other types of samples, liquids, etc.) from users (e.g., of the analytics system 100) such as farmers or other third parties (e.g., agriculture-related companies). In some embodiments, the analytics system 100 provides a sampling tube to a user, e.g., as part of a kit for collection of soil sample or related information. The user may collect a soil sample using the sampling tube and return the sampling tube (e.g., via mail or other delivery methods) to the analytics system 100 for processing. An interior of the sampling tube may be sterilized and may include a preservative solution, for example, to help maintain conditions of the soil sample or microbes present in the soil sample.

The analytics system 100 may determine a metric of a soil sample in view of a "crop community," that is, reference information associated with the soil sample. For example, the reference information includes data of other soil samples having similar conditions, in which same types of one or more crops were grown, treated with similar management or agricultural practices, or having other traits in common with the soil sample.

The analytics system 100 may provide metrics to users, e.g., for presentation on a client device 110 of a user. The analytics system 100 may also derive recommendations from metrics regarding agricultural techniques. Based on metrics or recommendations, farmers or other users may be informed as to a variety of actions that determine inputs or practices to use on fields, when to plant, where to plant, which crops to plant, or which varietals of those crops to plant, among other insights that may improve crop or soil health or performance. For example, the farmer may treat the soil in a particular way with a chemical, a fertilizer, one or more nutrients, one or more microbes, or other substances or components to adjust a characteristic of the soil or to modify the soil or its composition or microbiome. The farmer may take other actions to treat the soil to adjust its composition or characteristics, including mixing the soil, applying a different soil composition to the existing soil, among other changes or mechanisms for treatment.

A client device 110 comprises one or more computing devices capable of processing data as well as transmitting and receiving data over the network 130. For example, a client device 110 may be a desktop computer, a laptop computer, a mobile phone, a tablet computing device, an Internet of Things (IoT) device, or any other device having computing and data communication capabilities. The analytics system 100 may provide information to the client device 110 for presentation to a farmer or another user. The information may include metrics or recommendations determined by the analytics system 100 regarding soil samples or crops.

Though not shown in FIG. 1, the analytics system 100 may include one or more processors for manipulating and processing data, a network connection for communicating with other devices, and a non-transitory computer-readable storage medium for storing data, program code, or program instructions associated with various applications. It is noted that a storage medium may include volatile memory (e.g., random access memory) or non-volatile storage memory such as hard disks, flash memory, and external memory storage devices. The one or more processors may execute instructions to perform steps of one or more processes, e.g., the process described below with reference to FIG. 2A.

For purposes of explanation, this disclosure uses soil samples and the microbial composition of the soil samples generally as example use cases, though the embodiments described herein may be adapted for systems and methods using other types of biological samples or physical samples. For instance, the biological sample may be at least in part a liquid or aqueous sample used for growing plants in a hydroponics system. As a different example, the biological sample may be a sample of a gut microbiome of a subject (e.g., a human or another type of organism), and the analytics system 100 may determine metrics associated with physiology or other attributes of the subject.

II. EXAMPLE METHODS

Figure 2B:
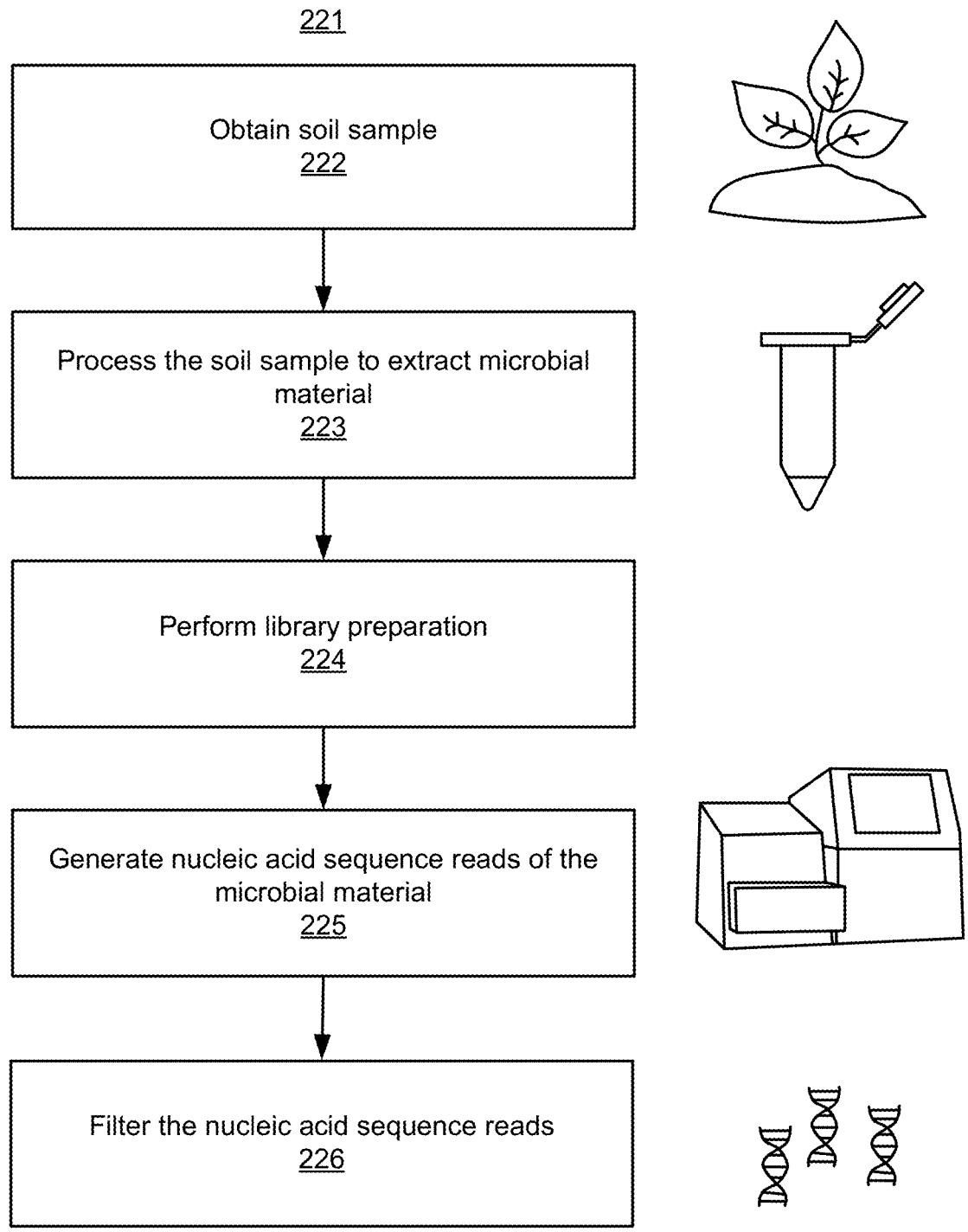
FIG. 2B illustrates an example process for generating sequence reads according to various embodiments of the present invention.

FIG. 2A illustrates an example process 200 for determining metrics of a soil sample according to various embodiments of the present invention. FIG. 2B illustrates an example process 221 for generating sequence reads according to various embodiments of the present invention. In various embodiments, the processes 200 or 221 are used by the analytics system 100 within the system environment in FIG. 1. The processes may include different or additional steps than those described in conjunction with FIG. 2A-B in some embodiments or perform steps in different orders than the order described in conjunction with FIG. 2A-B.

The analytics system 100 determines 202 (e.g., nucleic acid) sequence reads of a soil sample to which is added synthetic nucleic acids (e.g., a spike-in). Referring now to FIG. 2B, the process 221 may be performed to determine the sequence reads as part of the process 200 of FIG. 2A.

A soil sample is obtained 222 using any of the methods previously described with reference to FIG. 1, e.g., using a sampling tube. The soil sample is processed 223 to extract microbial material. In some embodiments, the soil sample may be stored at 4, −20, or −80 degrees Celsius, among other suitable temperatures, prior to extraction of the microbial material. In an embodiment, the soil samples are aliquoted into extraction vessels by mass, volume, suspension volume, or another measurement. A spike-in, such as a synthetic plasmid spike-in, is then added to the soil aliquot in a known amount. Cell lysis is performed on the soil samples with the added spike-in to release the microbial material including intracellular nucleic acids. Cell lysis methods may include chemical (buffers or salts), mechanical (bead beating or sonication), or thermal (e.g., freezing, free-thaw cycling, or microwaving) processes. Soil and the released microbial material are separated. Cellular debris may be removed using chemical precipitation, centrifugation, filtration, or binding, washing, or elution on a column or bead. Additionally, contaminants may be removed using precipitation or bead-based binding, followed by elution of the microbial material. The microbial material may be prepared using florescent dyes or gels for downstream assay or spectroscopy.

In some embodiments, the nucleic acids of the microbial material may be processed prior to library preparation. For example, target genes or genome regions may be enriched for polymerase chain reaction (PCR) amplification or amplicon sequencing. Targeted DNA primers may be used to flank a region of interest. Alternatively, in shot gun sequencing, the microbial material may be prepared for sequencing of the entire content, e.g., microbes in a crop community of the processed soil sample. In some use cases, DNA fragment size may be controlled chemically using size selection gel beads, physically using ultrasonic shearing, or enzymatically using transposase fragmentation.

Library preparation is performed 224 on the extracted microbial material. Library preparation may include attaching sequencing adapters or tags to nucleic acids to facilitate reading of the nucleic acids. Sequencing tags may be unique to each sample (e.g., serving as a barcode) and enable identification of sequenced data associated with each sample in a multiplexed run with multiple samples. In some use cases, library preparation includes protocols from sequencer original equipment manufacturers (OEMs), third party kit providers, or other resources.

Nucleic acid sequence reads of the microbial material are generated 225 using one or more techniques. In some embodiments, a sequencer performs sequencing (e.g., of DNA or RNA) and outputs sequence reads of the microbial material. The sequencer may provide the output sequence reads to the analytics system 100. The sequencer can be communicatively coupled to the analytics system 100 through a wireless, wired, or a combination of wireless and wired communication technologies. The analytics system 100 may use the sequence reads to identify presence or measure of one or more types of microbes in the soil sample. In some embodiments, the nucleic acid sequence reads are determined using next generation sequencing (NGS) techniques including synthesis technology (ILLUMINA®), pyrosequencing (454 LIFE SCIENCES), ion semiconductor technology (Ion Torrent sequencing), single-molecule real-time sequencing (PACIFIC BIOSCIENCES®), or nanopore sequencing (OXFORD NANOPORE TECHNOLOGIES).

The analytics system 100 filters 226 the nucleic acid sequence reads, e.g., for quality control. In particular, the analytics system 100 may remove sequence reads having artificial multiplexing barcode or adapter sequences. In addition, the analytics system 100 may determine that a sequence read is low quality responsive to determining that a length of the sequence read is less than a threshold value, the sequence read includes at least a threshold number of ambiguous bases, or a read quality score (e.g., determined using a third-party tool) is less than a threshold score. The analytics system 100 may discard low quality sequence reads. The analytics system may also partition sequence reads using identification barcodes for demultiplexing batches of sequence reads generated from multiple samples.

In other embodiments, instead of using nucleic acid sequencing, the analytics system 100 determines counts of organisms using quantitative PCR (qPCR) or Droplet Digital PCR (ddPCR).

Returning to FIG. 2A, the analytics system 100 classifies 204 the sequence reads, for example, into one or more subsets, where each subset is matched to a particular microbe present in the soil sample. The analytics system 100 can determine these classifications using information from a metagenomic reference database or other genomic databases to match sequence reads to known microbes. The analytics system 100 can also determine sequence reads that are classified to the spike-in added to the soil sample. Since the spike-in includes one or more artificially constructed sequences, the analytics system 100 can distinguish sequence reads of the spike-in from sequence reads of microbes. That is, sequence reads of microbes in the soil sample will match reference sequence reads of known microbes in one or more databases, while sequence reads from the spike-in in the soil sample are highly unlikely to have any matches in the databases.

The analytics system 100 assigns 206 a soil texture label to the soil sample according to one or more measures of texture of soil in the soil sample or a field where the soil sample was obtained. For example, the one or more measures includes percentages of sand, silt, and clay in the soil sample. In some embodiments, the sum of the percentages of sand, silt, and clay equals 100%.

Figure 8:
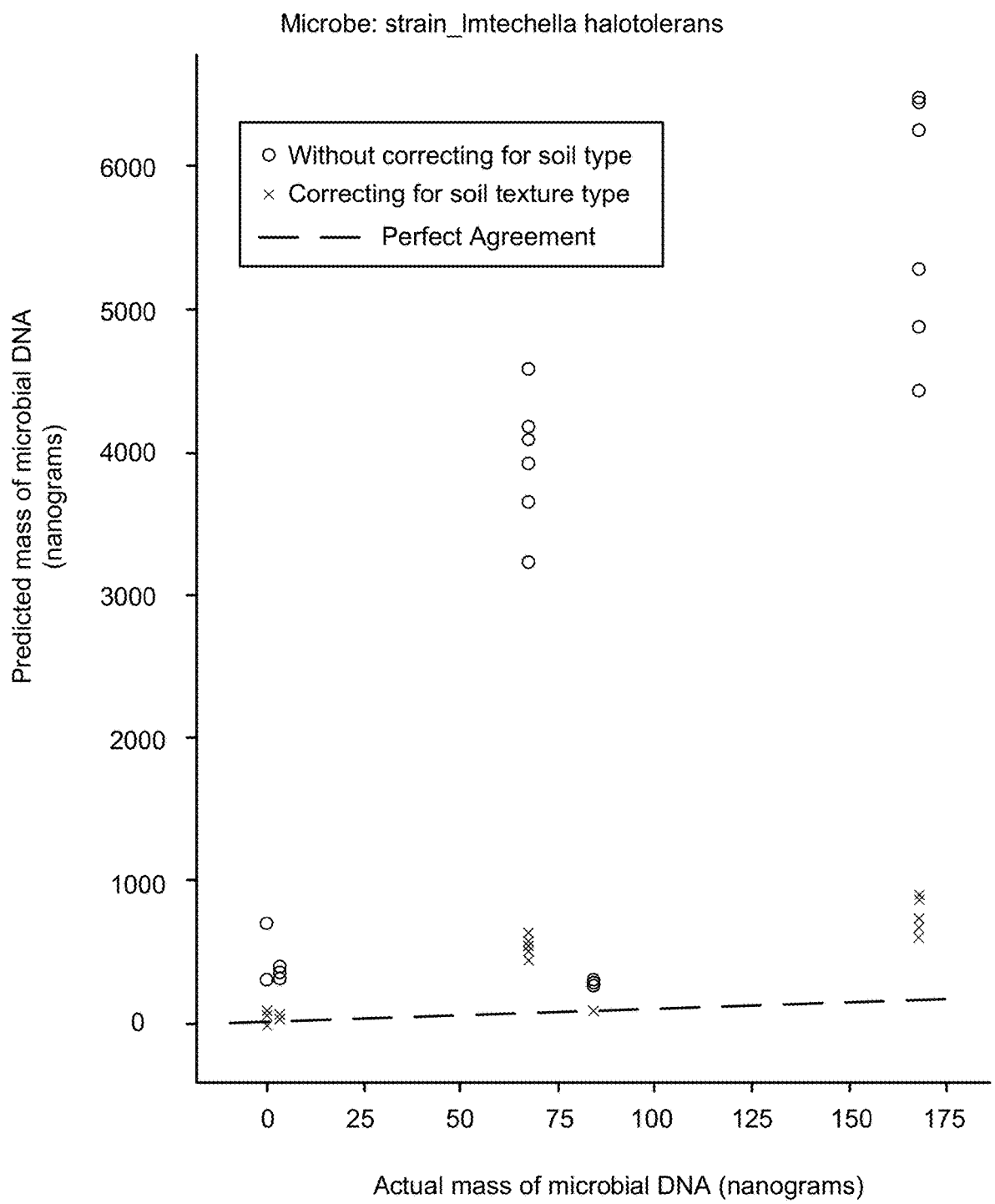
FIG. 8 is a diagram indicating predicted mass of a microbe accounting for soil texture type according to various embodiments of the present invention.
Figure 9:
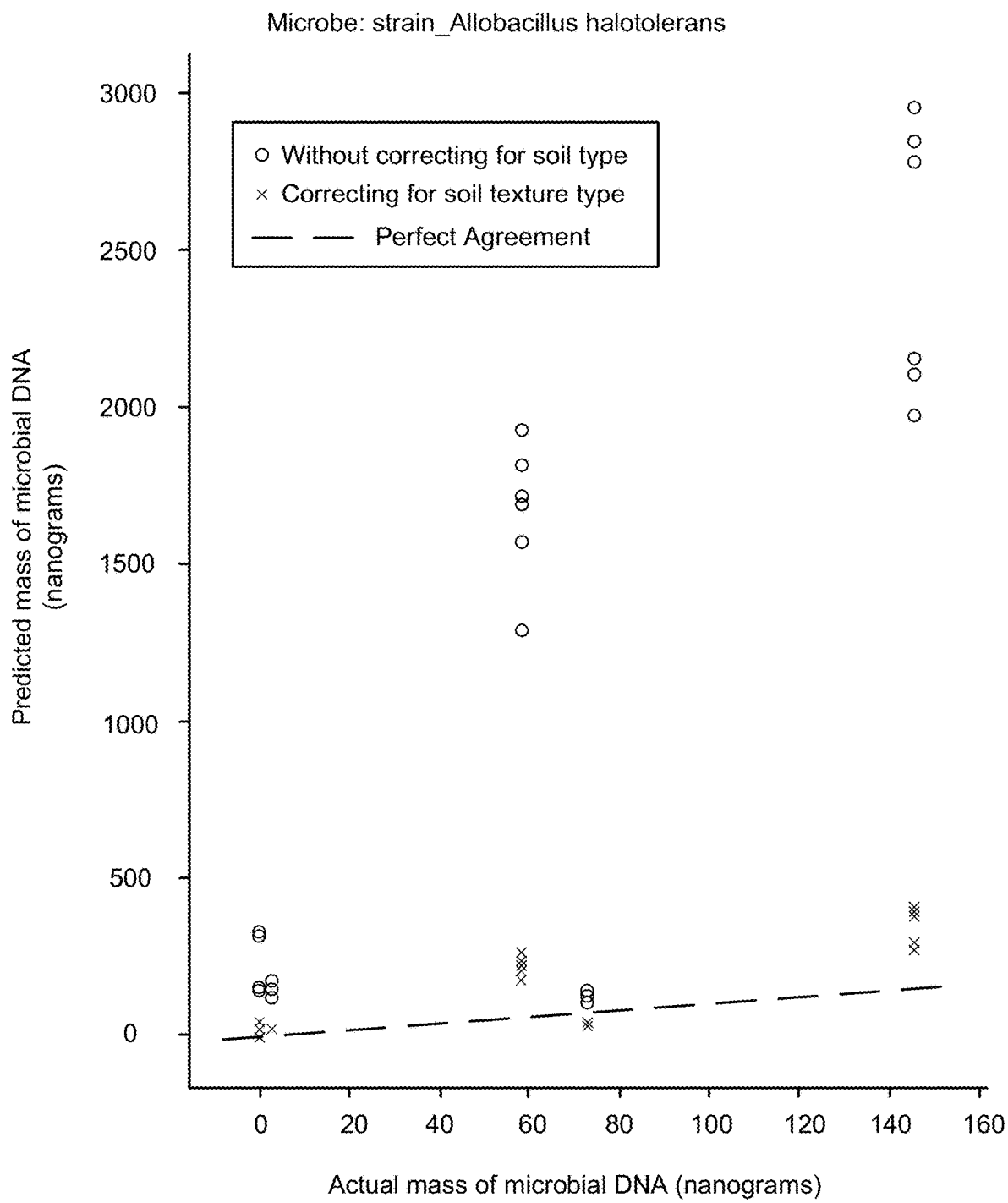
FIG. 9 is another diagram indicating predicted mass of microbe accounting for soil texture type according to various embodiments of the present invention.

The analytics system 100 determines 208 a measure of an amount of a microbe in the soil sample. The analytics system 100 can determine the measure as a function of at least the number of sequence reads matched to the microbe, the soil texture label, and a genomic mass of the spike-in. The analytics system 100 can account for the soil texture because physical properties of different compositions of sand, silt, and clay can affect extraction efficiency of nucleic acids from a soil sample. For example, soil samples with high clay content may result in reduced extraction efficiency of nucleic acids. Referring now to FIGS. 8-9, the diagrams shown in FIGS. 8-9 each indicate a predicted mass of a microbe determined by the analytics system 100. In both diagrams, the predicted mass of the microbe is more accurate (closer to perfect agreement with the actual mass of the microbe in the sample) when the analytics system 100 accounts for soil texture type.

In some embodiments, the measure is a genomic mass of the microbe, which is further described below. The genomic mass can be determined per unit of mass (e.g., grams) of the soil sample. In other embodiments, the measure is a cell count of the microbe in the soil sample per gram of the soil sample. The measure can also be a function of the number of sequence reads classified to the spike-in or one or more correction factors. The correction factors can account for underrepresented organism abundances. For instance, a correction factor is based on whether the microbe has a cell wall. As another example, a correction factor is based on cell lysis efficiency or classification efficiency.

In an embodiment, the analytics system 100 determines a value of a soil health indicator using the measure of the microbe. The soil health indicator may be a function of measures of one or more types of microbes, e.g., associated with oxygen status, nitrogen capacity, phosphorous capacity, potassium capacity, available carbon, plant growth promoting bacteria, root disease resistance, or post-harvest disease susceptibility. The analytics system 100 can determine microbial composition of the soil sample using the measure of the microbe. For example, the analytics system 100 determines measures of multiple microbes in the soil sample and aggregates the measures to determine the microbial composition of the soil sample.

The analytics system 100 transmits 210 the measure to a client device 110 for display on a user interface. Using the measure, users of the analytics system 100 may determine health or performance of their fields relative to other comparable fields in terms of geographical location, cropping history, soil treatments, among other traits encoded in metadata stored by the analytics system 100. The analytics system 100 may also store the measure in a database 120.

In an optional step in some embodiments, the soil sample or other soil is treated 212 according to the measure. For example, the metric may indicate that a crop is less resistant to root disease in comparison to an average metric of root disease for crops of the same or similar type, or crops grown in similar conditions or geographical locations. In response, a farmer may provide additional fertilizer or other types of substances to the crop or soil to mitigate possible negative effects of disease, or to modify levels of oxygen, nitrogen, phosphorous, potassium, or carbon of the soil. In one embodiment, the analytics system 100 may provide a command to a client device 110 or another type of device to automatically treat the soil with a treatment loaded onto the device. For instance, the device is a manned or autonomous tractor for applying fertilizer, water, or other substance to soil or crops. In some embodiments, step 212 includes providing a recommendation regarding how to treat the soil according to the metric.

III. SPIKE-IN

FIG. 3 is a diagram of relative abundance data of microbes in soil samples.

Relative abundance data may be misleading about numbers of microbes on an absolute scale present in soils. The chart on the left of FIG. 3 shows example distributions of a microbe of interest (indicated by dark shading) compared to a total biomass pool on an absolute scale across three different samples. The chart on the right of FIG. 3 shows corresponding data on relative abundance of the organisms for the three samples after sequencing. Absolute abundance of the organism in sample 2 is twice that of sample 1. However, the total mass of sample 2 is twice that of sample 1, so the relative abundances in samples 1 and 2 are equal. Additionally, the absolute abundances of the organism are equal in samples 1 and 3, but because sample 3 has a greater overall microbial population, the relative abundance appears lower in sample 3 than in sample 1.

Figure 4:
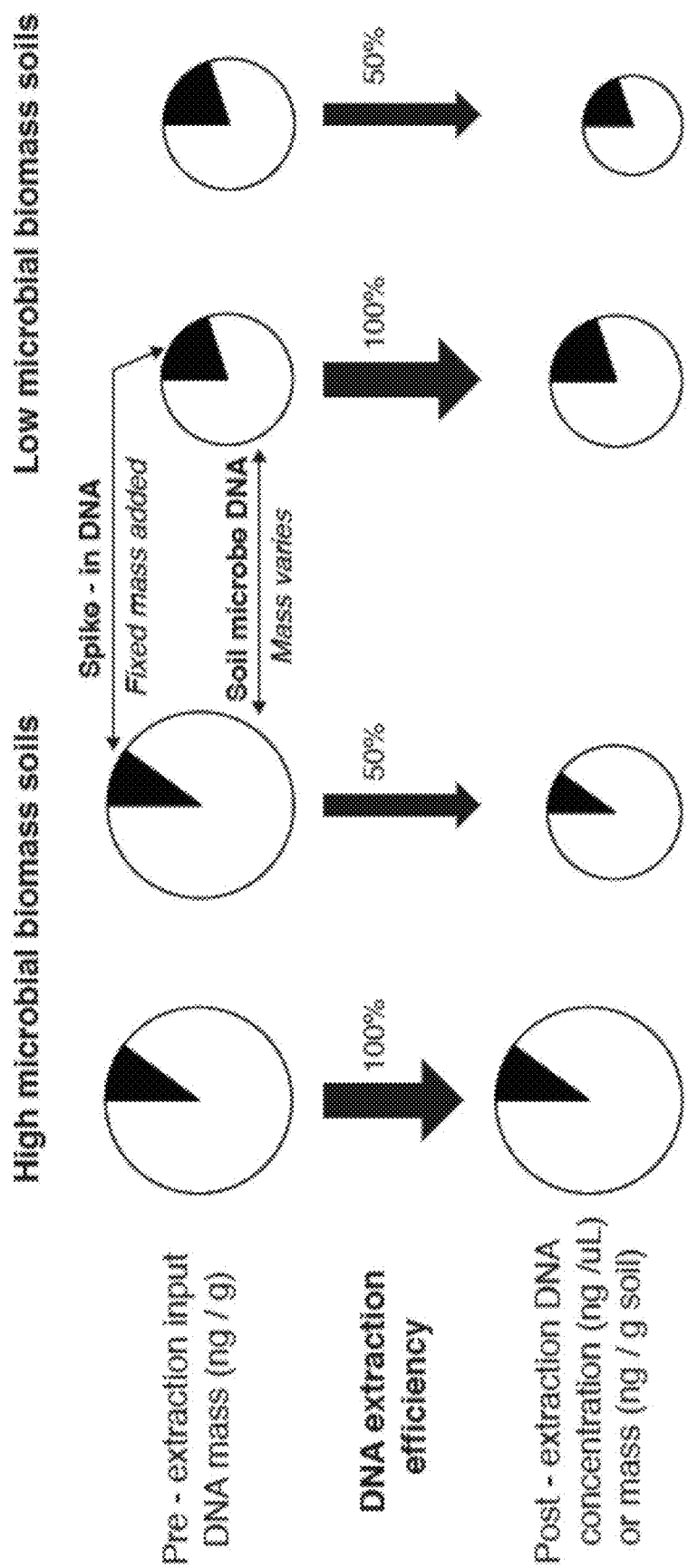
FIG. 4 is a diagram of proportions of a spike-in applied soil samples according to various embodiments of the present invention.

FIG. 4 is a diagram of proportions of a spike-in applied soil samples according to various embodiments of the present invention. The diagram illustrates conservation of synthetic spike-in proportions (indicated by dark shading) through DNA extraction across different initial biomass levels (indicated by the pie chart sizes) and extraction efficiencies. The synthetic spike-in is added at a fixed mass to a sample, and the spike-in becomes a proportion varying with the initial mass. Varying arrow thicknesses indicate different extraction efficiencies, with thicker arrows being more efficient DNA yield. Under these scenarios, the DNA yield post extraction (as indicated by the pie chart sizes) is not indicative of the initial sample mass, while the proportion of spike-in is independent of extraction yields. Thus, using post extraction DNA concentrations (or qPCR counts) may be misleading for estimating initial biomass.

On the other hand, a reads-based assessment of the proportion of DNA reads mapping to the synthetic spike-in is more proportional to the original mass. Estimation of the original mass of individual organisms may be determined using corrections for lysis and classification efficiencies, as further described below.

In various embodiments, a known constant amount (e.g., in ng of DNA) of a synthetic DNA plasmid spike-in is added to a soil sample prior to DNA extraction for sequencing. The synthetic DNA plasmid spike-in is an artificial sequence constructed with no significant detections in any metagenomic reference database, so that the spike-in is a highly unique piece of DNA that is nearly impossible to find in any natural metagenomic context. The spike-in may include three (or any other number of) constructs, each at different concentrations in a logarithmically-spaced ladder. Upon analysis of DNA sequence reads by taxonomic and or functional classification, the analytics system 100 may determine or enumerate the number of reads matching the synthetic constructs.

To account or correct for organisms or genes abundances from relative to absolute, the analytics system 100 assumes that the ratio of synthetic/total reads is proportionate to the ratios of their DNA masses in soil. Here, the analytics system 100 assumes that the composition of DNA is not substantially altered during the extraction or sequencing process, but rather DNA losses in the process are random with respect to their sequence identity. The analytics system 100 may determine absolute abundance of a given organism (e.g., ng genomic DNA/g soil or organisms/g soil) in part by using the ratio of plasmid reads to total reads as a proxy for the ratio of the initial mass of the organism to the (known) mass of plasmid added to soil, e.g., subject to one or more correction factors.

The analytics system 100 may modify quantitation of organisms using correction factors applied from additional data. As one example, a correction factor relates to classification rates of sequence reads (i.e., percentage of reads identified as organisms). For instance, where 50% of reads are identified as any organism, a simple ratio of identified reads to plasmid reads will under-represent the absolute abundance of all microbes by one half. The classification rate of the synthetic DNA construct is also of interest, though may also be nearly 100% due to the unique sequence identity of the spike-in/construct.

For correction of the initial overall community DNA mass, the analytics system 100 may determine the classification rate as the percentage of reads classified. However, when considering the abundances of organisms individually (e.g., a given pathogen), the analytics system 100 may also account for variation in the organism's individual classification rate. The analytics system 100 may derive the individual classification rate from sequencing data from physical organisms or in-silico experiments where simulated sequence reads are constructed from whole genome sequence data.

The analytics system 100 can compute the genomic mass (or biomass) of an organism as follows:

$$\frac{m_i}{m_p} = \frac{\frac{n_i}{\varepsilon_c}}{n_p}$$

Here, $m_i$ represents the genomic mass of the organism i of concern, $m_p$ represents the (known) genomic mass of the synthetic plasmid spike-in, $n_i$ represents the number of reads classified to organism i, $n_p$ represents the number of reads classified to the synthetic spike-in, and $\varepsilon_c$ represents the average classification efficiency across all organisms detected, though individual classification rates may also be substituted. The ratio $n_i/\varepsilon_c$ represents the correction for under-represented microbial abundances aforementioned. From the above formula, the analytics system 100 can calculate the desired quantity, $m_i$, and the mass of genomic DNA from organism i present in the sample. With a known genome size and ploidy of organism i, the analytics system 100 can also calculate the number of cells/organisms of organism i present in the sample.

In some embodiments, the analytics system 100 can apply a correction factor to $n_p$ based on one or more measures of soil texture of the soil sample. The analytics system 100 can also apply a correction factor to $n_p$ to account for batch effects or theoretical recall of sequence reads. For example, the analytics system 100 multiplies $n_p$ by a factor of five to account for a change in concentration of the spike-in due to a laboratory lot change. This factor can be determined by comparing shift in biomass between control samples and test samples using a new spike-in lot. In other embodiments, the factor can be a number different than five, depending on variations across laboratories or processes. In some embodiments, the analytics system 100 normalizes the genomic mass according to dry mass content of the soil sample.

Figure 7:
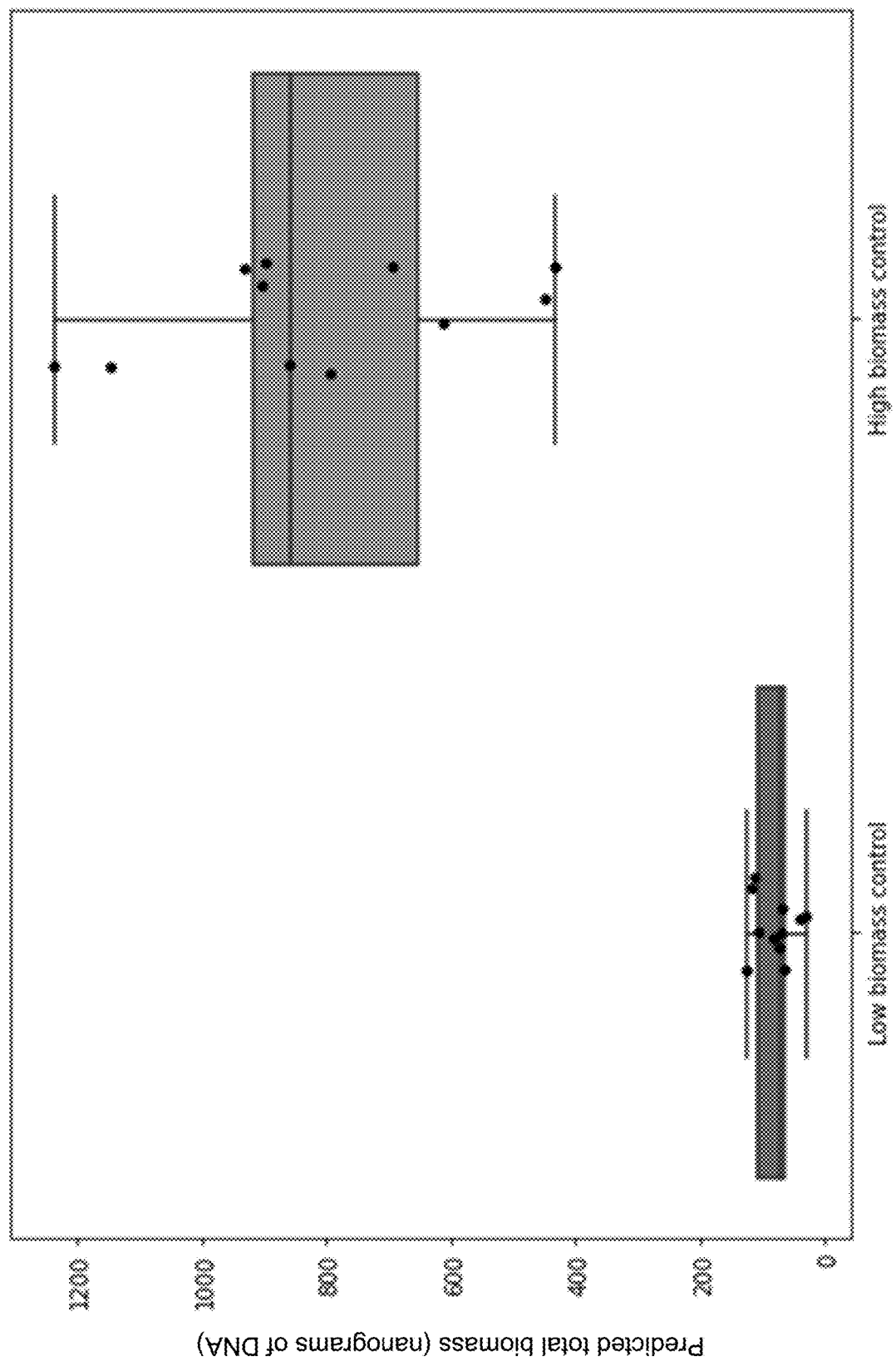
FIG. 7 is a diagram indicating total biomass of control samples according to various embodiments of the present invention.

Referring now to FIG. 7, FIG. 7 is a diagram indicating total biomass of control samples according to various embodiments of the present invention. The analytics system 100 determine the total biomass of a soil sample (in nanograms of DNA) by aggregating predicted mass of microbes in the soil sample. The analytics system 100 can determine the total biomass and predicted mass of each the microbes using any combination of the correction factors or other methods described herein. In the example shown in FIG. 7, the low biomass control has a theoretical biomass of 157 nanograms, and the high biomass control has a theoretical biomass of 1048 nanograms. The example predictions of total biomass for both the low and high biomass controls are close to the corresponding theoretical biomass. Although, there is more variation in the predictions for the high biomass control than in the predictions for the low biomass control.

Figure 13:
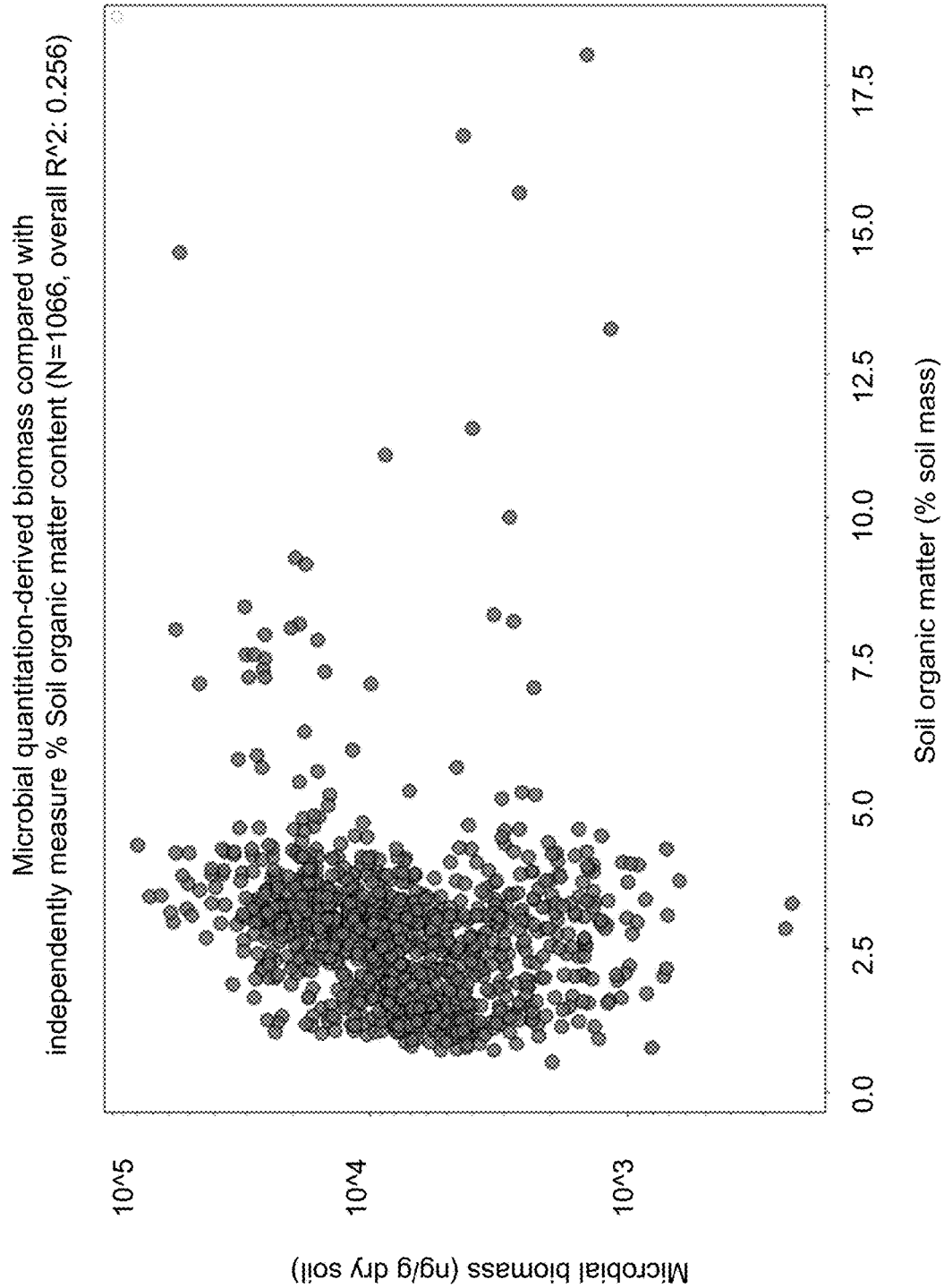
FIG. 13 is a diagram of microbial quantitation-derived biomass according to various embodiments of the present invention.

Referring now to FIG. 13, FIG. 13 is a diagram of microbial quantitation-derived biomass according to various embodiments of the present invention. As shown in FIG. 13, total microbial biomass (in nanograms per gram of dry soil) as determined by the analytics system 100 tracks with the soil organic matter up to a saturation point (e.g., 2.5-5% in value). The analytics system 100 can estimate total biomass of microbial genetic material present in a soil sample by measuring the amount of all microbes present in the soil sample. In some embodiments, the analytics system 100 can account for environmental perturbations (e.g., fumigation, fungicide treatments, pillaging, etc.) when determining total biomass. As an example use case, the analytics system 100 can use the total biomass to determine genomic mass of a microbe per a unit of mass of the soil sample. In addition, the analytics system 100 can use total biomass to normalize a measure of an amount of a microbe. In some embodiments, the analytics system 100 can use total biomass as a proxy for elemental masses (e.g., carbon or nitrogen).

In some embodiments, the analytics system 100 applies a correction factor to account for variation in cell lysis efficiencies of soil organisms. The proportion of plasmid:total reads (or identified reads) may be proportionate to the mass of plasmid DNA to soil DNA pre-extraction. However, the read proportion may reflect only DNA proportions from sequencing libraries after extraction and lysing, which may be skewed by incomplete cell lysis, and moreover may vary by microbial taxa or cell wall composition (e.g., the mycoplasma genus of bacteria does not have cell walls). For example, if 50% of microbial community DNA is released during cell lysis, then the ratio of microbial DNA:plasmid (and resulting mass ratio calculations) will be similarly skewed to under-represent the initial DNA mass by two fold. Moreover, if a particular group is preferentially lysed (e.g., gram negative versus gram positive bacteria with cell walls instead of membranes), for example, at twice the rate of another, the apparent absolute abundance of the particular group will be similarly overrepresented by two-fold.

The analytics system 100 determines correction factors for lysis efficiency using spike-ins of known organisms at known masses to either water or soils, along with the plasmid spike-in. The analytics system 100 may determine the lysis efficiency of these organisms by accounting for the known mass of their DNA added to soils or liquids, compared to the mass amount estimated relative to the synthetic plasmid as described previously. The analytics system 100 can calculate lysis efficiency from the difference in input versus calculated masses of organisms or organism classes.

IV. CORRECTION FACTORS

Figure 5:
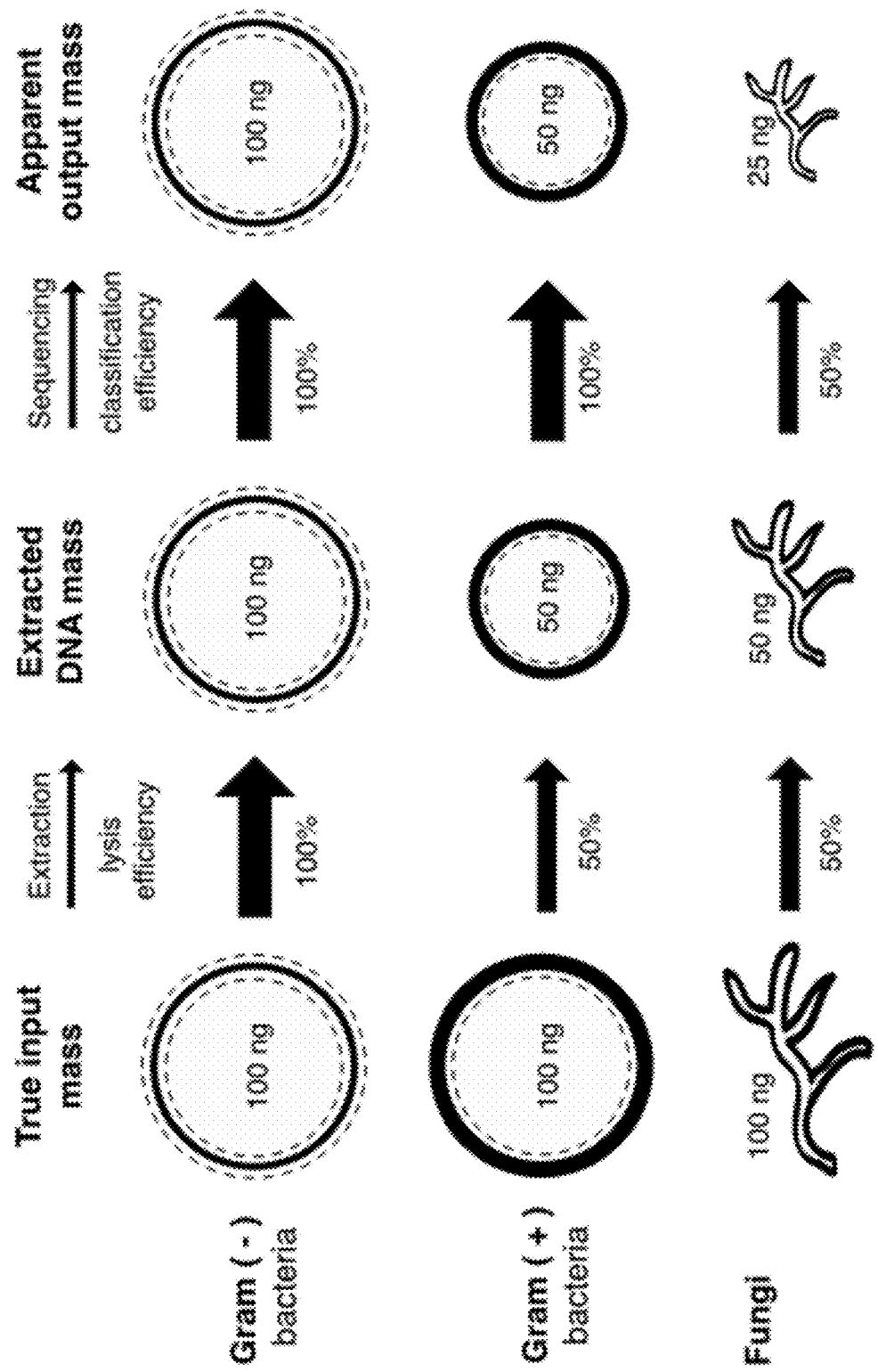
FIG. 5 is a diagram of correction factors for quantitation of organisms according to various embodiments of the present invention.

FIG. 5 is a diagram of correction factors for quantitation of organisms according to various embodiments of the present invention. In particular, FIG. 5 illustrates correction for three example classes of organisms: Gram negative (Gram −, no cell wall), Gram positive (Gram +, has cell wall), and fungi (with different cellular structures). The diagram illustrates apparent loss in counts of these organism classes (by size of drawing) due to different efficiencies in cell lysis or bioinformatics classification. Thickness of the arrows indicates relative cell lysis efficiency (thicker arrows correspond to higher efficiencies). Decreasing cell sizes indicate loss of signal. Here, Gram − bacteria have greater lysis efficiency than either Gram + or fungi, such that their apparent numbers are greater in sequence data. While classification efficiency of Gram − and + organisms may be approximately equal, fungi have lower classification and lysis efficiencies. Thus, the analytics system 100 may use correction factors for both lysis efficiency and classification efficiency (reflecting use of taxonomic marker gene amplicon sequencing) so that fungi measurements based on sequence data more accurately reflect their abundances in source soils.

V. TREATMENT

FIG. 6 is a diagram illustrating that calculation of organism mass in soils from corrected sequence data shows the effect of fungicide on soil fungi and specific fungal plant pathogens, where uncorrected sequencing data alone does not. Application of a microbial spike-in and other corrections to derive biomass from sequence data may alter agronomic conclusions compared to sequence data alone. FIG. 6 shows how this correction alters the interpretation of effects of a fungicide treatment applied to soils in order to control fungal plant pathogens. Plots to the left of FIG. 6 (the Sequence relative abundance plots for all fungi, fungal pathogen 1, and fungal pathogen 2) illustrate that, when you are considering only the relative abundance of organisms as a percentage of sequence reads, no effect of the fungicide is detectable for all fungi, or two examples pathogenic species (pathogens 1 and 2). However, following calculation of organisms' mass using the synthetic spike-in (as an estimator of input soil DNA mass) and other factors, the fungicide treatment has clearly reduced the mass abundance of all fungi, and of the two pathogen species (right side panels of FIG. 6 under Corrected mass).

VI. EXAMPLE USER INTERFACE LAYOUTS

Figure 11:
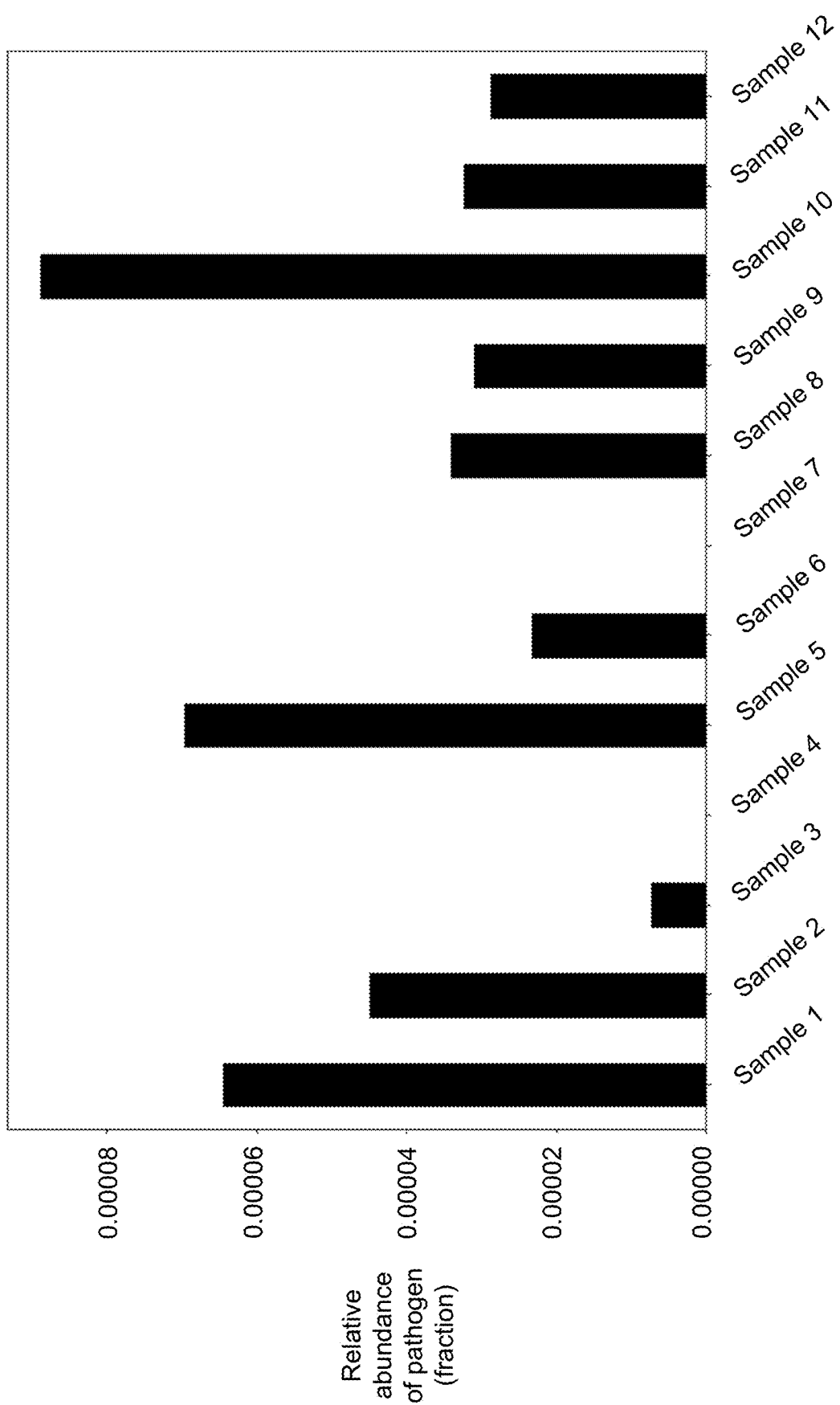
FIG. 11 is a diagram indicating relative abundance of the pathogen shown in FIG. 10 according to various embodiments of the present invention.

The analytics system 100 can use determined measures of microbes to generate information for display in a user interface on a client device. In various use cases, an agronomist or a farmer can view or interact with the user interface to inform decisions regarding management of a field. By considering the measures of microbes provided by the analytics system 100, the agronomist or farmer can determine whether and where it would be effective to apply treatment to soil. For instance, a treatment can be applied responsive to determining that a threshold amount of a certain bacteria is present in soil samples from the field. FIG. 10 is a diagram indicating microbial quantitation of a pathogen according to various embodiments of the present invention. FIG. 11 is a diagram indicating relative abundance of the pathogen shown in FIG. 10 according to various embodiments of the present invention. The example shown in FIG. 10 includes absolute abundance of a corn pathogen (in nanograms of DNA per gram of soil) as determined by the analytics system 100. The absolute abundance of the corn pathogen is greater than the illustrated threshold (0.60 parts per billion in soil) in four of the samples. By comparison, the example shown FIG. 11 includes relative abundance of the corn pathogen in the same samples. Using measures of absolute abundance instead of, or in addition to, measures of relative abundance can be advantageous. As previously described with reference to FIG. 3, using relative abundance data alone can mask useful information regarding an amount of a microbe in a sample or field.

Figure 12:
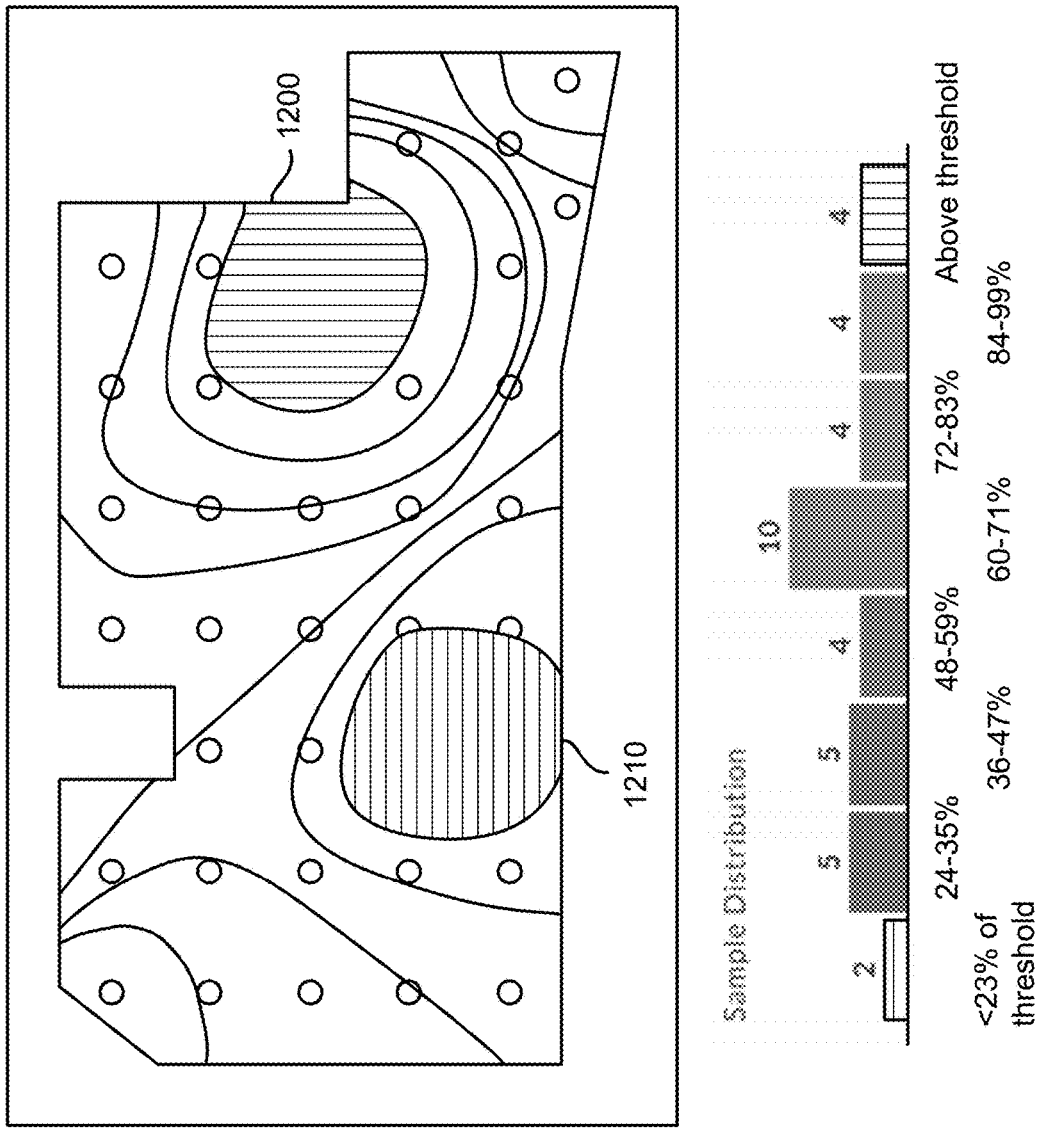
FIG. 12 illustrates a user interface layout including metrics of soil samples according to various embodiments of the present invention.

FIG. 12 illustrates a user interface layout including metrics of soil samples according to various embodiments of the present invention. In the example shown in FIG. 12, the user interface layout includes a topographical heatmap of a field. The heatmap illustrates distribution of a soilborne fungus (*Fusarium virguliforme*) that can cause sudden death syndrome in soybean plants. The area 1200 of the heatmap corresponds to a distribution of the fungus that is above a threshold. A different area 1210 of the heatmap corresponds to a distribution of the fungus that is less than 23% of the threshold. As illustrated by the heatmap, the analytics system 100 can enable targeted treatment of soil by providing granular measures of microbes in a field. Here for example, a farmer can apply more treatment to the area 1200 of the field that has a greater distribution of the fungus.

VII. ADDITIONAL CONSIDERATIONS

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A system comprising:
   a sampling tube for obtaining a soil sample to which is added one or more synthetic nucleic acids; and
   a non-transitory computer readable storage medium having instructions that when executed by one or more processors cause the one or more processors to:
   determine a plurality of sequence reads of the soil sample;

classify the plurality of sequence reads into one or more subsets, each subset matched to a particular microbe present in the soil sample;

assign to the soil sample a soil texture label according to one or more measures of texture of soil in the soil sample;

determine a measure of an amount of a microbe within the soil sample as a function of at least a subset of the plurality of sequence reads matched to the microbe, the soil texture label assigned, and a mass of the one or more synthetic nucleic acids present in the soil sample; and transmit the measure of the microbe within the soil sample to a client device for display on a user interface.

2. The system of claim 1, wherein assign to the soil sample the soil texture label comprises:

determine a first percentage of sand in the soil sample;

determine a second percentage of silt in the soil sample; and determine a third percentage of clay in the soil sample, wherein the first percentage, second percentage, and third percentage sum to 100%.

3. The system of claim 1, wherein determine the measure of the amount of the microbe comprises:

normalize the measure of the amount of the microbe according to dry mass content of the soil sample.

4. A method comprising:

determining a plurality of sequence reads of a soil sample to which is added one or more synthetic nucleic acids;

classify the plurality of sequence reads into one or more subsets, each subset matched to a particular microbe present in the soil sample;

assign to the soil sample a soil texture label according to one or more measures of texture of soil in the soil sample;

determining a measure of an amount of a microbe within the soil sample as a function of at least a subset of the plurality of sequence reads matched to the microbe, the soil texture label assigned, and a mass of the one or more synthetic nucleic acids present in the soil sample; and transmitting the measure of the microbe to a client device for display on a user interface.

5. The method of claim 4, wherein assigning to the soil sample the soil texture label comprises:

determining a first percentage of sand in the soil sample;

determining a second percentage of silt in the soil sample; and determining a third percentage of clay in the soil sample, wherein the first percentage, second percentage, and third percentage sum to 100%.

6. The method of claim 4, wherein determining the measure of the amount of the microbe comprises:

normalizing the measure of the amount of the microbe according to dry mass content of the soil sample.

7. The method of claim 4, further comprising:

performing cell lysis on the soil sample after the one or more synthetic nucleic acids has been added and before determining the plurality of sequence reads of the soil sample.

8. The method of claim 4, wherein the one or more synthetic nucleic acids includes a plurality of synthetic nucleic acids each at different a concentration.

9. The method of claim 4, wherein the measure of the amount of the microbe is a genomic mass of the microbe per a unit of mass of the soil sample, and wherein determining the measure of the amount of the microbe comprises:

determining a ratio of a first number of sequence reads in the subset of the plurality of sequence reads matched to the microbe to a second number of sequence reads of the plurality of sequence reads matched to the one or more synthetic nucleic acids.

10. The method of claim 9, wherein the ratio includes at least one correction factor accounting for underrepresented organism abundances.

11. The method of claim 10, wherein the at least one correction factor is based on whether the microbe has a cell wall.

12. The method of claim 10, wherein the at least one correction factor is based on cell lysis efficiency or classification efficiency.

13. The method of claim 4, wherein the measure of the amount of the microbe is a cell count of the microbe in the soil sample per gram of the soil sample.

14. The method of claim 4, further comprising:

treating a field where the soil sample was obtained according to the measure of the amount of the microbe.

15. The method of claim 4, further comprising:

determining a total biomass of microbial genetic material present in the soil sample by measuring amounts of a plurality of microbes present in the soil sample.

16. A non-transitory computer readable storage medium having instructions that when executed by one or more processors cause the one or more processors to:

determine a plurality of sequence reads of a soil sample to which is added one or more synthetic nucleic acids;

classify the plurality of sequence reads into one or more subsets, each subset matched to a particular microbe present in the soil sample;

assign to the soil sample a soil texture label according to one or more measures of texture of soil in the soil sample;

determine a measure of an amount of a microbe within the soil sample as a function of at least a subset of the plurality of sequence reads matched to the microbe, the soil texture label assigned, and a mass of the one or more synthetic nucleic acids present in the soil sample; and transmit the measure of the microbe to a client device for display on a user interface.

17. The non-transitory computer readable storage medium of claim 16, wherein assign the soil texture label comprises:

determine a first percentage of sand in the soil sample;

determine a second percentage of silt in the soil sample; and determine a third percentage of clay in the soil sample, wherein the first percentage, second percentage, and third percentage sum to 100%.

18. The non-transitory computer readable storage medium of claim 16, wherein the one or more synthetic nucleic acids includes a plurality of synthetic nucleic acids each at different a concentration.

19. The non-transitory computer readable storage medium of claim 16, wherein the measure of the amount of the microbe is a genomic mass of the microbe per a unit of mass of the soil sample, and wherein determine the measure of the amount of the microbe comprises:

determine a ratio of a first number of sequence reads in the subset of the plurality of sequence reads matched to the microbe to a second number of sequence reads of the plurality of sequence reads matched to the one or more synthetic nucleic acids.

20. The non-transitory computer readable storage medium of claim 19, wherein the ratio includes at least one correction factor accounting for underrepresented organism abundances, and wherein the at least one correction factor is based on whether the organism has a cell wall, cell lysis efficiency, or classification efficiency.

\* \* \* \* \*